United States Patent

Förster

4,171,568
Oct. 23, 1979

[54] ARCH WIRE RETAINER

[75] Inventor: Rolf Förster, Pforzheim, Fed. Rep. of Germany

[73] Assignee: Firma Bernhard Förster, Pforzheim, Fed. Rep. of Germany

[21] Appl. No.: 847,415

[22] Filed: Oct. 31, 1977

[30] Foreign Application Priority Data

Jan. 17, 1977 [DE] Fed. Rep. of Germany ....... 2701716
Oct. 1, 1977 [DE] Fed. Rep. of Germany ....... 2744283

[51] Int. Cl.² .............................................. A61C 7/00
[52] U.S. Cl. ............................................... 32/14 A
[58] Field of Search ................... 32/14 A, 14 R, 14 C

[56] References Cited

U.S. PATENT DOCUMENTS

| | | | |
|---|---|---|---|
| 1,613,114 | 1/1927 | Linde | 32/14 A |
| 2,011,575 | 8/1935 | Ford | 32/14 A |
| 2,046,414 | 7/1936 | Russell | 32/14 A |
| 2,318,001 | 5/1943 | Linde | 32/14 A |
| 2,959,856 | 11/1960 | Gurin | 32/14 A |
| 3,087,244 | 4/1963 | Heuttner et al. | 32/14 A |
| 3,158,934 | 12/1964 | Waldman | 32/14 A |
| 3,238,619 | 3/1966 | Brunson et al. | 32/14 A |
| 4,077,126 | 3/1978 | Pletcher | 32/14 A |
| 4,103,423 | 8/1978 | Kessel | 32/14 A |

Primary Examiner—Louis G. Mancene
Assistant Examiner—Michael J. Foycik, Jr.

[57] ABSTRACT

A bracket has a longitudinal channel adapted to receive a wire arch. A retaining member is rotatably mounted in the bracket body and includes a retaining spider which is angularly movable to first and second retaining positions, in which the retaining spider extends across at least part of the width of the passage. The retaining spider is adapted in the first retaining position to slidably retain a wire arch in the channel and in the second retaining position to clamp a wire arch in position in the channel.

20 Claims, 14 Drawing Figures

Fig. 1

ARCH WIRE RETAINER

This invention relates to a bracket for retaining wire arches of orthodontic appliances.

Known brackets for retaining wire arches of orthodontic appliances have grooves in which the wire arches are retained by means of tying wires or U-shaped wire clips. The tying wires or clips must be removed and re-applied when such known bracket is to be adjusted in accordance with the progress of the orthodontic treatment. It is difficult to remove the tying wires or clips and to re-apply them in the mouth of the patient. Besides, the bracket must be exchanged when the treatment requires a wire arch consisting of wire having a different thickness, or when a wire arch is required which consists of round-section wire, to be slidably retained, rather than of rectangular-section wire which is adapted to be clamped in position. The tying wires are applied around wire-retaining wings of the known brackets and are then twisted together to tighten the bracket. When a change is required, the tying wires must be cut open and new wires must subsequently be applied. This is complicated and time-consuming.

It is an object of the invention to provide for wire arches of orthodontic appliances a retaining bracket which can be applied and re-adjusted with ease and can be used throughout the time of the treatment. The bracket according to the invention comprises a bracket body having a longitudinal channel for receiving a wire arch, which is adapted to be slidably retained or to be clamped in position by a retaining disk or spider which is rotatably mounted on the base member and has portions which are pivotally movable to retaining positions over the channel. This design facilitates the re-adjustment of slidably or fixedly retained wire arches without need for a re-tightening of tying wires.

The rotatable retaining disk may consist of an eccentric disk, which is rotatably mounted on the pin and has a retaining portion having an upwardly inclined underside surface. That retaining portion is pivotally movable to a position for slidably retaining the wire arch which has been inserted in the channel, and to a position for clamping said wire arch in position. Alternatively, a spider may be used, which has a rotatably mounted stub shaft and pivotally movable arms which differ in thickness so that selected arms are pivotally movable to a position over the longitudinal channel to slidably retain the wire arch inserted therein, or to clamp said wire arch in position.

To control the axial position of the rotatable disk or spider, the free end of the shaft can be held in the bracket body by a snubbing spring riveted to the stub shaft.

According to a further feature of the invention, the bracket according to the invention comprises a bracket body having a longitudinal channel for receiving a wire arch, and a rotatable retaining disk having pivotally movable retaining portions for slidably retaining the wire arch and for clamping it in position. The disk is provided with a shaft that is rotatably mounted in the bracket body and an eccentric disk for laterally clamping the wire arch is associated with the retaining disk. The eccentric disk may be integral with the shaft and be pivotally movable into the longitudinal channel from the side. The retaining disk is disposed in a recess of the bracket body and is cut off on one side to facilitate the operation of the bracket. Improved results can be produced in accordance with a further feature of the invention by the provision of a tandem bracket, which comprises two bracket bodies, each of which is provided with a rotatable holding-down disk and a laterally clamping eccentric disk.

Further details of the invention will now be described more fully with reference to the accompanying drawings, in which preferred embodiments are shown diagrammatically and by way of example.

Each of the brackets shown in FIGS. 1 to 4 comprises a bracket body 1 having a longitudinal channel 2 for receiving a correcting arch. A rotatable spider 4 having pivotally movable spider arms 5 serves to slidably retain the correcting arch or to clamp it in position. To enable this, the pivotally movable spider arms have different thicknesses, indicated at "d", and the spider is rotatable to move a selected spider arm to a position in which it extends across the longitudinal channel 2 in which the correcting arch 3 has been inserted.

Figure 1:
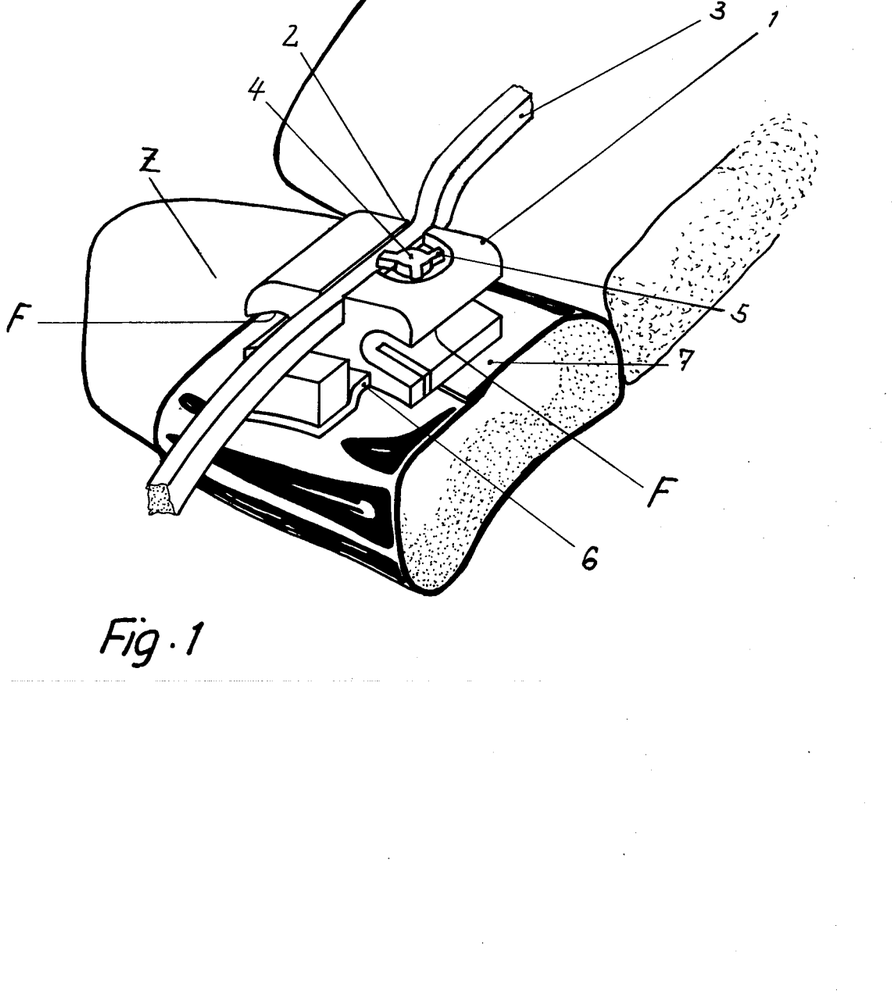
FIGS. 1 and 2 show respective brackets provided with a rotatable spider and wire-retaining wings in conjunction with correcting wire arches.
Figure 2:
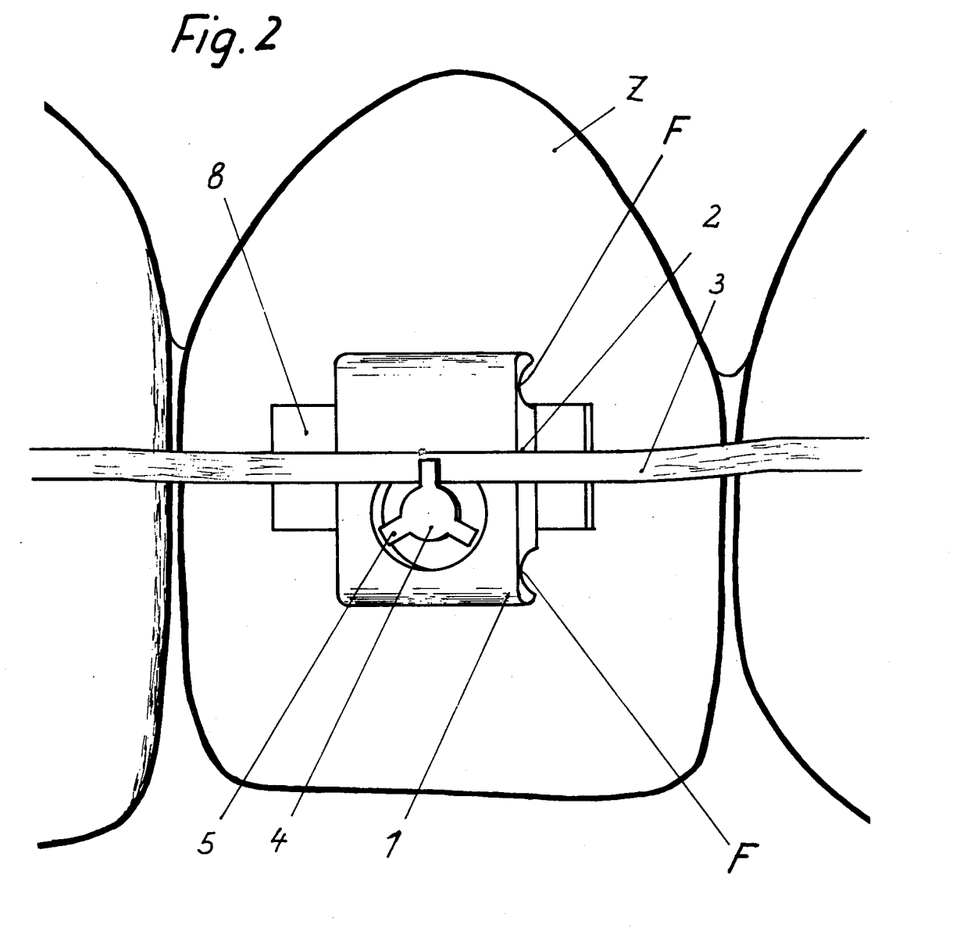

In the first embodiment, shown in FIG. 1, the bracket consists of two parts, including a fit-in tongue 6, and is mounted by means of the latter on a metal strap 7, which is wrapped around the tooth Z and is held on the latter by the bracket. The bracket clamps the correcting arch 3 and urges it labially against the tooth Z. The bracket according to the second embodiment, shown in FIG. 2, has a base plate 8, which acts in an oral direction relative to the tooth Z.

Figure 3:
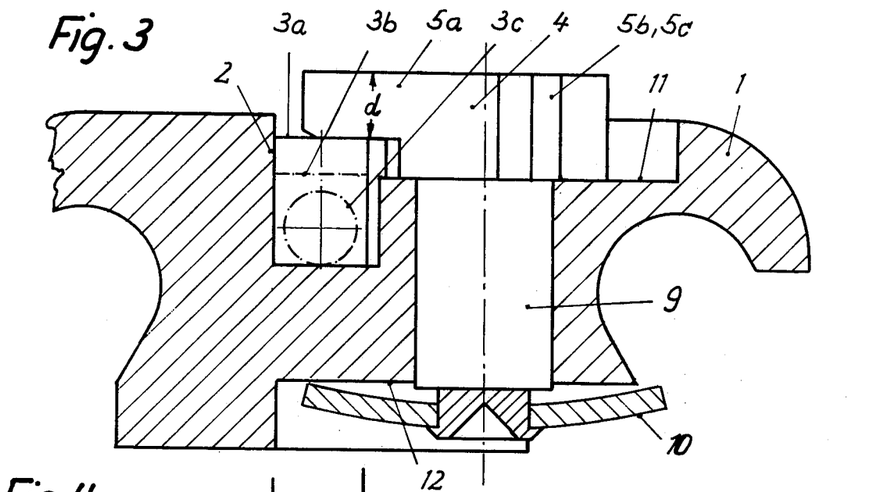
FIGS. 3 and 4 are, respectively, a fragmentary view, partly in cross-section, and a top plan view showing the clamping device of FIG. 2 on an enlarged scale.
Figure 4:
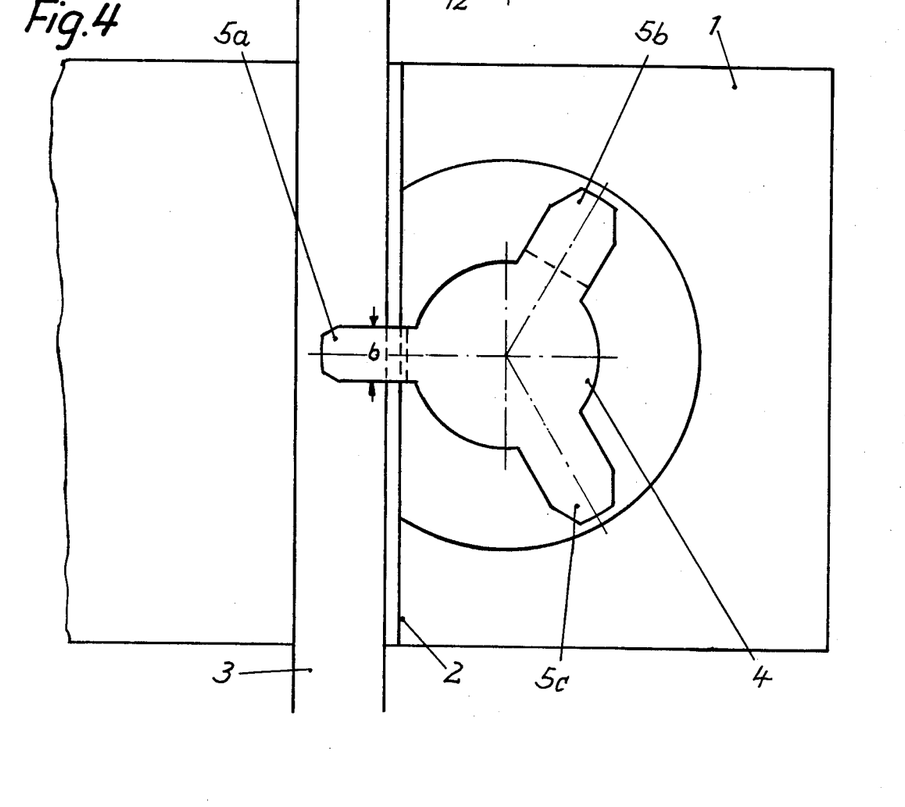

As in apparent from FIGS. 3 and 4, the second embodiment comprises a rotatable spider 4, which is rotatably mounted in the bracket body 1 by a stub shaft 9. A snubbing spring 10 is riveted to the free shaft end and tends to hold the shaft in a predetermined axial position. The spider 4 and the snubbing spring 10 are disposed in respective recesses 11 and 12 of the bracket body 1. It is apparent from FIG. 3 that the pivoted arms 5a have different thicknesses "d" for cooperating with different correcting arches 3a to 3c.

Figure 7A:
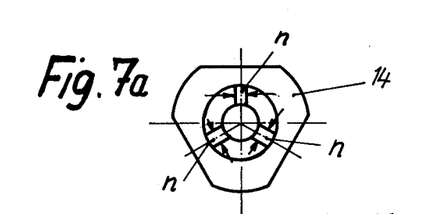
FIGS. 7a and 7b show a wrench for adjusting the bracket according to FIG. 1.
Figure 7B:
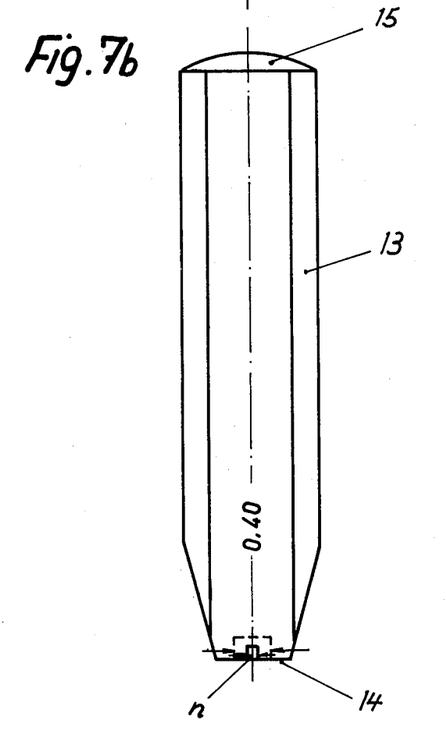

It is apparent from FIG. 4, the pivoted arms 5a to 5c may also differ in width "b" so that the position to which the rotatable spider of the small bracket has been adjusted by means of a wrench 13, shown in FIGS. 7a and 7b, is readily apparent. The wrench 13 has at its lower end 14 three grooves having different widths "n" and is correspondingly marked at its top 15. When the correcting arch has been inserted into the bracket body, the rotatable spider can readily be adjusted by means of the wrench 13 to positions for slidably retaining the correcting arch and for clamping it in position.

Figure 5:
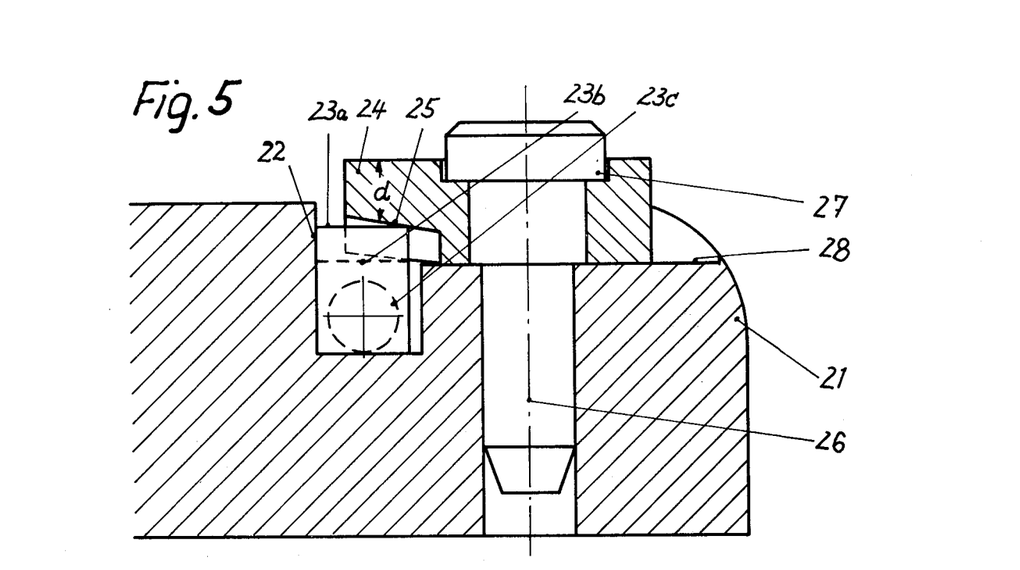
FIGS. 5 and 6 are fragmentary view, partly in cross-section, and a top plan view showing another embodiment.
Figure 6:
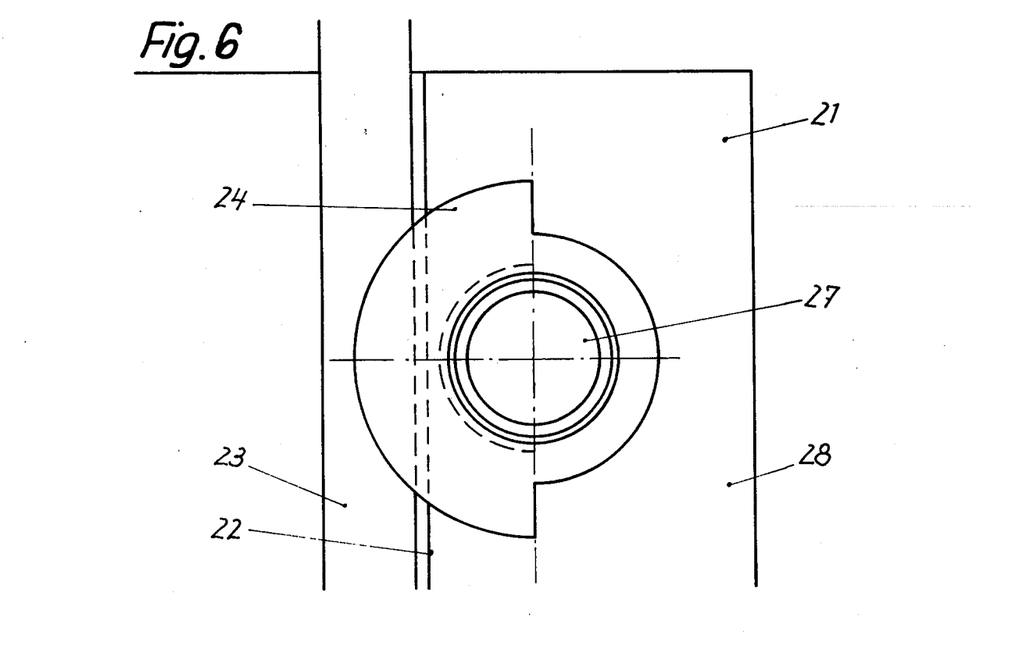

The bracket shown in FIGS. 5 and 6 comprises a bracket body 21 having a longitudinal channel 22 for receiving correcting arches 23a to 23c. A rotatable eccentric disc 24 is provided, which has an inclined bottom face 25, and is movable so that a portion having a desired thickness "d" extends across the longitudinal channel 22 and a correcting arch 23a to 23c disposed in said longitudinal channel can thus be retained. The eccentric disc 24 is mounted on a stub shaft 26, which is axially fixed in the bracket body 21 and has a head 27, which holds down the disk 24, which is disposed on a recessed surface 28 of the bracket body. This bracket represents a modification of the last preceding embodiment in that it is apparent from the angular position of the eccentric disk whether it is in a position for slidably retaining a correcting arch in the passage or in a position for clamping said wire arch in position.

To provide for a stronger retaining force, two bracket bodies according to the invention may be disposed one behind the other or, for retaining two parallel correcting arches, one above the other. In such arrangement, each bracket body may be provided with wire-retaining wings F, which define longitudinal side grooves and may be used to secure correcting arches by means of wire loops. This is necessary, e.g., when the teeth are set back to such an extent that the arch cannot be clamped in the manner shown in FIG. 1 or 2.

Figure 8:
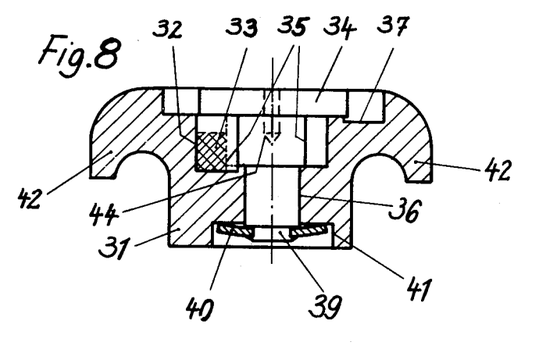
FIGS. 8 to 10 are, respectively, a transverse sectional view, a top plan view and a side elevation showing another bracket.
Figure 9:
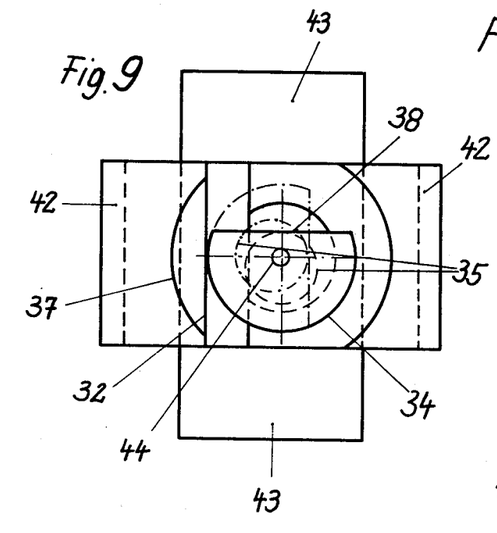
Figure 10:
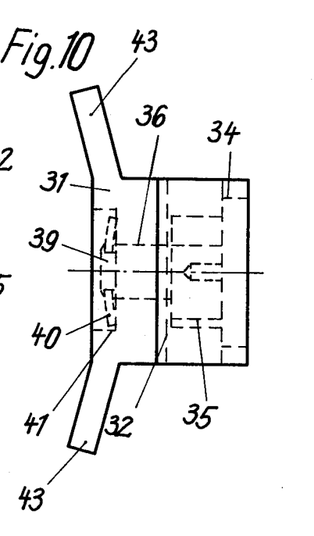

The bracket shown in FIGS. 8 to 10 comprises a bracket shown in FIGS. 8 to 10 comprises a bracket body 31 having a longitudinal channel 32 for receiving a correcting arch 33. The rotatable retaining member comprises a rotatable head 34 and an eccentric retaining disk 35, which is pivotally movable to positions for slidably retaining the correcting arch 33 in the longitudinal channel 32 and for clamping the correcting arch in position. One angular position of the eccentric disk 35 is indicated by dash-dot lines in FIGS. 8 and 9. The rotatable retaining member is rotatably mounted in the bracket body 31 by a stub shaft 36. The generally round head 34 is received in a recess 37 of the bracket body and has a flat 38, which permits of an insertion of the correcting arch 33 into the longitudinal channel 32 and of an operation of the rotatable clamping member by means of a wrench. This design results in a compact assembly.

The rotatable retaining member is held in a predetermined axial position by means of a snubbing spring 40, which is riveted to the stub shaft 36 at 39 and is disposed in a suitable recess 41 of the bracket body 31 and curved toward the latter. The bracket body 31 is also provided with wire-retaining wings 42. Side lugs 43 formed integrally with the bracket body serve to secure the latter to the tooth strap, which is not shown here.

Figure 13:
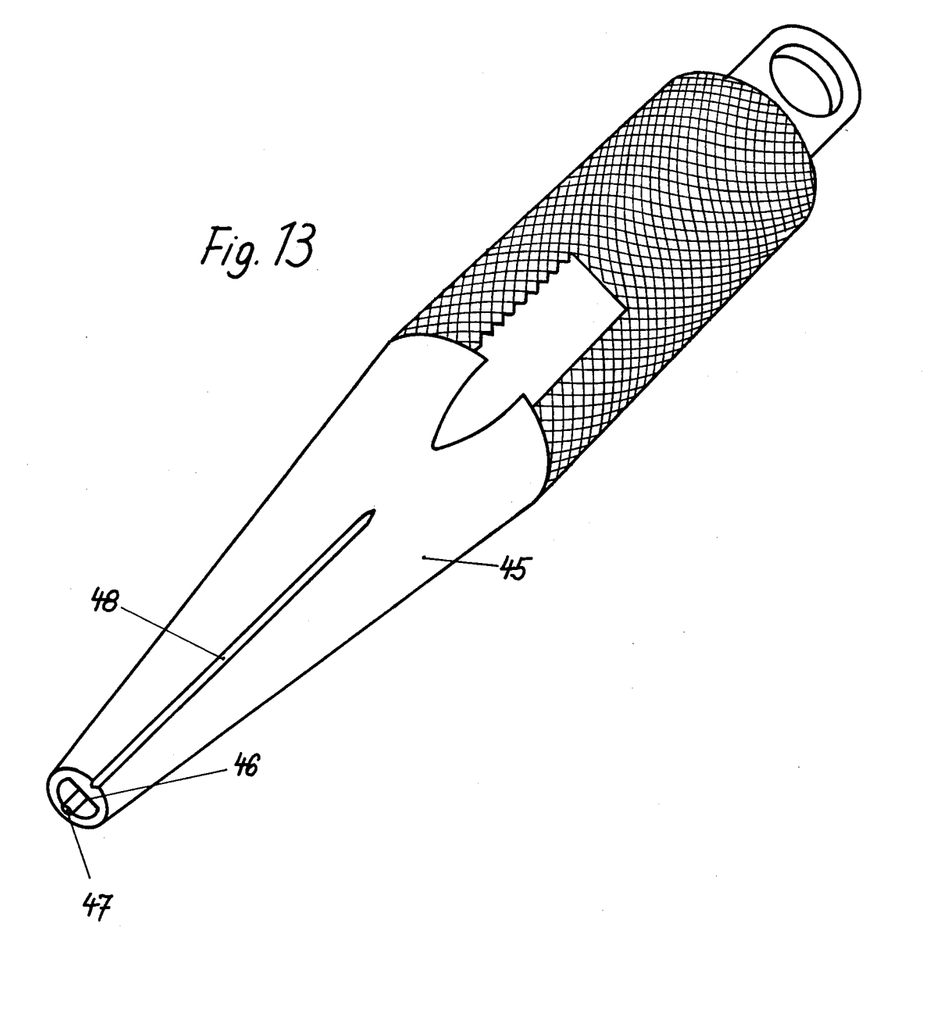
FIG. 13 is a perspective view showing a wrench for operating the bracket.

The rotatable head 34 is movable to a position in which it extends across the longitudinal channel 32 to slidably retain the correcting arch 33 in said channel. Close to the flat 38, the rotatable head 34 has a central bore 44, which is adapted to receive a socket wrench 45, shown in FIG. 13 for rotating the head 34. The socket wrench 45 comprises a lateral flat 46 and a protruding central pin 47 which facilitates the application of the socket wrench to the rotatable head 34. An exposed indicating notch 48 is provided on the outside of the socket wrench 45.

Figures 11, 12:
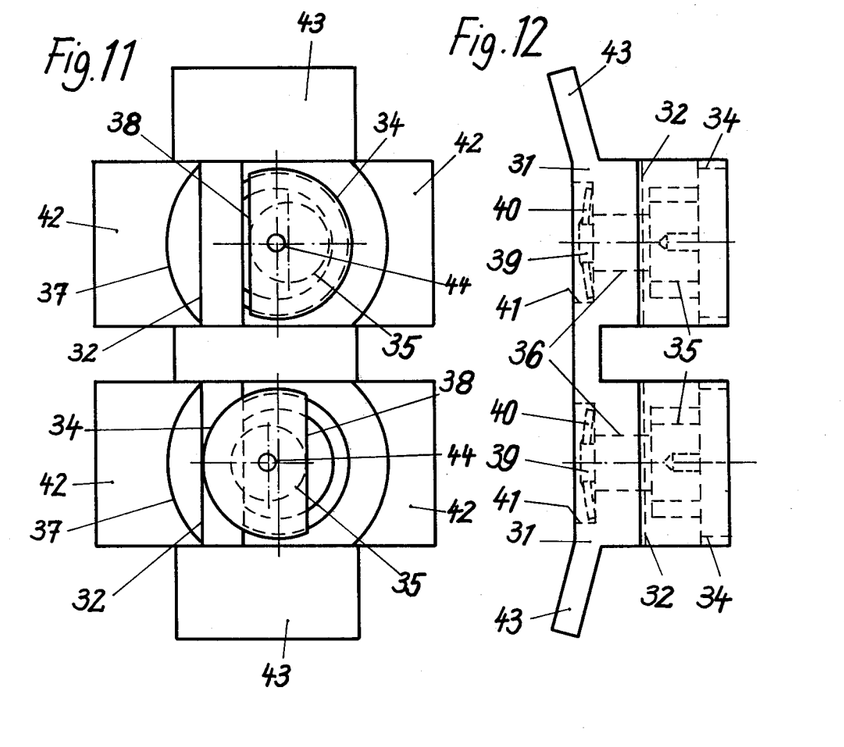
FIGS. 11 and 12 are, respectively, a top plan view and a side elevation showing a tandem bracket.

FIGS. 11 and 12 show a tandem bracket which comprises two brackets of the type shown in FIGS. 8 to 10. This arrangement results in a more reliable fixation. The two eccentric retaining disks 35 are shown in different positions.

What is claimed is:

1. A bracket for retaining an orthodontic wire arch, comprising
   at least one bracket body having a longitudinal channel adapted to receive a wire arch on one side thereof, and a recess on the other side thereof opposite to said channel, and
   at least one retaining member which is rotatably mounted in said bracket body and comprises a shaft extending into said recess in said bracket body, retaining means which are angularly movable to first and second retaining positions in which said retaining means extend across at least part of the width of said channel and means for securing said shaft in said bracket body so as to locate said retaining member in a predetermined axial position relative to said bracket body, said retaining means and said channel being disposed on one side of said bracket body, opposite said recess, said retaining means being adapted in said first retaining position to slidably retain a wire arch in said channel and in said second retaining position to clamp a wire arch in position in said channel.

2. A bracket as set forth in claim 1, in which said retaining means comprise a disk which is movable to said first and second retaining positions.

3. A bracket as set forth in claim 1, in which said retaining means comprise a spider, which is movable to said first and second retaining positions.

4. A bracket as set forth in claim 1, in which said retaining means are axially fixed to said shaft which is rotatably mounted in said bracket body, and
   said securing means comprise a snubbing spring, which is secured to said shaft and frictionally engages said bracket body and urges said retaining means axially against said bracket body, so that said retaining means are movable into retaining and clamping positions across said channel.

5. A bracket as set forth in claim 4, in which said spring is riveted to said shaft.

6. A bracket as set forth in claim 5, in which,
   said shaft extends through said bracket body, and
   said spring is disposed in said recess and is curved toward said bracket body, for securing said shaft in said bracket body in a pre-determined axial position.

7. A bracket as set forth in claim 1, in which said bracket body is formed with wire-retaining wings.

8. A bracket as set forth in claim 1, in which
   said retaining means comprise angularly spaced apart first and second surface portions which axially face said bracket body and are axially offset from each other,
   said first surface portion is movable to a position in which said first surface portion extends across at least part of the width of said channel and is then adapted to slidably retain a wire arch in said channel, and
   said second surface portion is movable to a position in which said second surface portion extends across at least part of the width of said channel and is then adapted to clamp a wire arch in position in said channel.

9. A bracket as set forth in claim 1, in which said retaining means comprise a spider having a thinner and a thicker spider arm formed with said first and second surface portions, respectively.

10. A bracket as set forth in claim 9, in which said spider arms differ in width.

11. A bracket as set forth in claim 8, in which said retaining means comprise a retaining disk formed with said first and second surface portions.

12. A bracket as set forth in claim 1, in which
said longitudinal channel has a lateral aperture and
said retaining member further comprises an eccentric disk which is arranged to extend through said aperture into said channel and to laterally clamp a wire arch in said channel, when said retaining means is in said second retaining position.

13. A bracket as set forth in claim 12, in which said eccentric disk is non-rotatably connected to said shaft which is rotatably mounted in said bracket body so that said retaining means are angularly movable to said first and second retaining positions for retaining and clamping respectively a wire arch in said channel.

14. A bracket as set forth in claim 12, in which said retaining member further comprises a head formed with a lateral flat, which is engageable to rotate said retaining member, so as to permit an insertion of a wire arch into said channel.

15. A bracket as set forth in claim 12, in which said retaining member comprises an exposed end formed with a lateral flat which is engageable by a wrench for rotating said retaining means.

16. A bracket as set forth in claim 15, in which said exposed end is formed with a central bore, which is engageable by an axially protruding, locating pin of said wrench.

17. A bracket as set forth in claim 1, in which said retaining member comprises an exposed end formed with a central bore, which is engageable by a locating pin of a wrench for rotating said member.

18. A bracket as set forth in claim 17, in which said retaining member is formed at said exposed end with a lateral flat for engagement by a wrench for rotating said member.

19. A bracket as set forth in claim 1, in which said bracket body has side lugs for fixation to a tooth strap.

20. A bracket as set forth in claim 1, in which
two of said bracket bodies are connected so that said longitudinal passages are longitudinally aligned and
two of said retaining members are provided, each of which is rotatably mounted in one of said bracket bodies.

* * * * *